US010588810B2

(12) United States Patent
Brown et al.

(10) Patent No.: US 10,588,810 B2
(45) Date of Patent: Mar. 17, 2020

(54) LUMBAR TRACTION DEVICE

(71) Applicants: Kelley Brown, Leander, TX (US); Mark L. Berrier, Austin, TX (US)

(72) Inventors: Kelley Brown, Leander, TX (US); Mark L. Berrier, Austin, TX (US)

( * ) Notice: Subject to any disclaimer, the term of this patent is extended or adjusted under 35 U.S.C. 154(b) by 533 days.

(21) Appl. No.: 15/240,908

(22) Filed: Aug. 18, 2016

(65) Prior Publication Data

US 2017/0049656 A1 Feb. 23, 2017

Related U.S. Application Data

(60) Provisional application No. 62/207,308, filed on Aug. 19, 2015.

(51) Int. Cl.
*A61F 5/048* (2006.01)
*A61H 1/02* (2006.01)

(52) U.S. Cl.
CPC ... *A61H 1/0222* (2013.01); *A61H 2201/1253* (2013.01); *A61H 2201/1284* (2013.01); *A61H 2203/0456* (2013.01); *A61H 2205/081* (2013.01)

(58) Field of Classification Search
CPC ...... A61H 2203/0456; A61H 2205/081; A61H 2201/1253; A61H 2201/1284; A61H 1/0292; A61H 1/0222; A61F 5/04; A61F 5/042; A61F 5/048; A47C 1/02; A47C 1/024; A61G 13/1225; A61G 13/123
See application file for complete search history.

(56) References Cited

U.S. PATENT DOCUMENTS

| | | | | |
|---|---|---|---|---|
| 2,120,310 | A | 6/1938 | Duncan | |
| 3,258,790 | A | 7/1966 | Maru | |
| 4,285,081 | A | 8/1981 | Price | |
| 4,383,342 | A * | 5/1983 | Forster | A47C 7/405 297/284.1 |
| 4,603,689 | A * | 8/1986 | Homer | A61H 1/0218 602/32 |
| 5,024,214 | A * | 6/1991 | Hayes | A61H 1/0218 482/95 |
| 5,467,490 | A | 11/1995 | Rice | |
| 7,568,248 | B2 | 8/2009 | Nakayama | |
| 8,769,744 | B1 | 7/2014 | Brown | |
| 9,241,586 | B1 | 1/2016 | Brown | |

FOREIGN PATENT DOCUMENTS

| | | | |
|---|---|---|---|
| EP | 2 016 926 | A1 * | 1/2009 |

* cited by examiner

*Primary Examiner* — Anna K Kinsaul
*Assistant Examiner* — Camtu T Nguyen

(57) ABSTRACT

Systems and methods for providing traction to the lower back, where in one embodiment, a lumbar traction device has a back support, a base and a movable support structure connected between the base and the underside of the back support. The support structure enables the back support to move with respect to the base. When a user lies on the lumbar traction device, the user's weight causes the back support to move with respect to the base to apply tension to the user's back. The back support may have two separate portions on which the upper and lower back rest. The two portions of the back support move in opposite directions to provide traction on the back.

7 Claims, 2 Drawing Sheets

LUMBAR TRACTION DEVICE

CROSS-REFERENCE TO RELATED APPLICATIONS

This application claims the benefit of U.S. Provisional Patent Application 62/207,308, filed Aug. 19, 2015 by Kelley Brown et al., which is incorporated by reference as if set forth herein in its entirety.

BACKGROUND

Field of the Invention

The invention relates to systems and methods for applying traction to the lower part of the back.

SUMMARY OF THE INVENTION

This disclosure is directed to systems and methods for applying traction to a person's lower back. One embodiment comprises a lumbar traction device that has a back support, a base and a movable support structure connected between the base and the underside of the back support. The support structure enables the back support to move with respect to the base. When a user lies on the lumbar traction device, the user's weight causes the back support to move with respect to the base to apply tension to the user's back. The back support may have two separate portions on which the upper and lower back rest. The two portions of the back support move in opposite directions to provide traction on the back.

An alternative embodiment comprises a method for applying traction to a person's lower back. In this embodiment, a device having a back support is provided, where the back support is connected to a movable support structure that rests on a base, so that the back support is movable with respect to the base. A user is positioned on the device (lies down on the device) so that the user's hips rest on the base and the user's back rests on the back support. The user's hips are held in position on the base (e.g., by gravity and friction between the user's hips and the base). The user's weight causes the back support to move in a direction away from the hips so that it applies traction to the user's back (slightly pulls the back away from the hips).

Numerous other embodiments are also possible.

BRIEF DESCRIPTION OF THE DRAWINGS

Other objects and advantages of the invention may become apparent upon reading the following detailed description and upon reference to the accompanying drawings.

Figure 1:
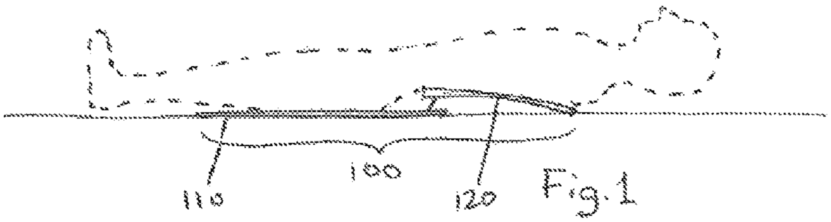
FIG. 1 is a diagram illustrating the use of one embodiment of a lumbar traction device.

While the invention is subject to various modifications and alternative forms, specific embodiments thereof are shown by way of example in the drawings and the accompanying detailed description. It should be understood, however, that the drawings and detailed description are not intended to limit the invention to the particular embodiment which is described. This disclosure is instead intended to cover all modifications, equivalents and alternatives falling within the scope of the present invention as defined by the appended claims. Further, the drawings may not be to scale, and may exaggerate one or more components in order to facilitate an understanding of the various features described herein.

DETAILED DESCRIPTION OF EXEMPLARY EMBODIMENTS

This disclosure is directed to various methods and apparatus for applying traction to the lower back or lumbar region of a person's body. The disclosed embodiments are intended to be illustrative of the invention.

Many people suffer from back pain that may be relieved, at least in part, by applying traction to the lower back. "Traction" is used here to refer to the application of a slight tension to pull one part of the body away from another part of the body. More specifically, in regard to the lower back, tension is applied to pull the upper vertebrae and discs away from the lower vertebrae and discs. It is noted that the tension will not be great, and the actual movement of the vertebrae and discs will be very slight, but the goal is to relieve compression of the vertebrae and the discs between them.

Referring to FIG. 1, a diagram is shown to illustrate the use of one embodiment of a lumbar traction device. This figure, a person's body is shown by the dashed line. The person is in a reclined position on top of lumbar traction device 100, which is positioned on a supporting surface such as the floor. Lumbar traction device 100 is shown in more detail in FIG. 2. It can be seen that the person's lower body (from the waist down) is lying on top of a first part (110) of the device. The weight of the lower body on this part of the device keeps it stationary on the supporting surface. In other words, on 110 does not move on the supporting surface. Part 110 may be referred to as the base of the device.

The person's torso rests on a second part (120) of the lumbar traction device. This component of the device may be referred to as a back support, upper back support or torso support. Back support 120 is connected to base 110 by a movable support structure 130. In this embodiment, base 110 is a flat structural member, and the lower end of movable support structure 130 is hingedly (pivotally) connected to base 110, while the upper end of the movable support structure is hingedly (pivotally) connected to back support 120. The weight of the person's torso on back support 120 causes the end of the back support is connected to movable support structure 130 to move downward. As movable support structure 130 pivots on base 110, the upper end of this structure, and consequently back support 120 moves away from base 110 (toward the right side of the figure). The positions of back support 120 and movable support structure 130 after the person's weight is applied to these structures is shown by the dashed lines in FIG. 2. It can be seen that back support 120 moves slightly downward and to the right in the figure.

Because the person's lower body is stationary on base 110, movement of back support 120 to the right in the figure applies tension to the person's lower back which is intended to decompress the vertebrae and discs in the lower back.

Figure 2:
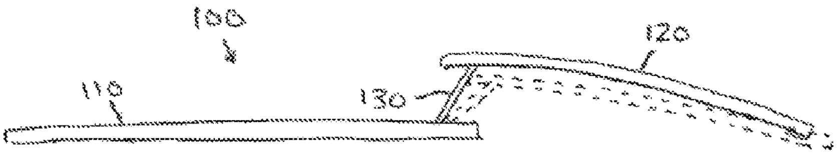
FIG. 2 is a diagram illustrating a first exemplary embodiment of a lumbar traction device.

In this embodiment, movable support structure 130 is spring-loaded so that, when no weight is applied to the device, it will be in the position shown in solid lines in FIG. 2. As the person's weight is applied to back support 120, movable support structure 130 will be pivoted clockwise or the position shown by the dashed lines. When the person's weight is removed, movable support structure 130 will return to the slightly more upright position shown by the solid lines. It should be noted that the spring loading may be provided in a number of ways, such as through the use of springs in contact with a rigid, but pivoting upright member, or through the use of a flexible movable support member that is connected to the back support without a hinge or pivot. Still other means of implementing the movable support member are possible.

It should also be noted that back support 120 can be designed to maintain essentially the same orientation as it moves under the person's weight, or it may be designed to slightly change its orientation as it moves. Back support 120 (as well as base 110) may incorporate materials, surfaces, shapes, etc. that improve the ergonomics of the device (e.g., make the device more comfortable for the person), and that facilitate the functioning of the device (e.g., gripping the person's body enough to provide tension between the lower body and the torso). Many other variations may be possible as well. These variations apply not only to the embodiments of FIGS. 1 and 2, but also to the other embodiments disclosed herein.

The diagrams of FIG. 1 and FIG. 2 are intended to illustrate the general structure and function of the lumbar traction device. The illustrated structures are very simple and do not picked some of the features which may be incorporated into the device. For example, the particular shapes of base 110 and back support 120 may be designed to conform to the contours of the person's body, rather than being simple, flat or slightly curved surfaces. The use of a more contoured shape may help prevent the person's body from slipping on these surfaces, which might use the amount of traction that is provided. Base 110 and back support 120 may also incorporate cushioning, non-slip surfaces, and other features that enable the device to more effectively transfer of the tension (produced by movement of back support 120 away from base 110) to the person's body.

Figure 3:
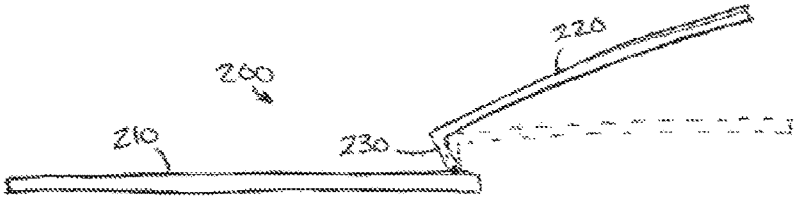
FIG. 3 is a diagram illustrating a second exemplary embodiment of a lumbar traction device.

Referring to FIG. 3, an alternative embodiment of a lumbar traction device is shown. In this embodiment, a stationary base 210 is similar to base 110 of FIG. 2, but the movable support structure (230) and the back support (220) are combined into a rigid structure, rather than being movable with respect to each other. It can be seen in FIG. 3 that support structure 230 and back support 220 form an "L" shape. When back support 220 is raised, support structure 230 is angled slightly to the left of vertical. When a person's weight is applied to back support 220, the back support is pushed downward, which causes it and support structure 230 to pivot clockwise. As support structure 230 pivots clockwise, the upper end of this structure moves slightly to the right, moving the back support away from base 210. If the person's lower body is stationary on base 210, the person's torso (on back support 220) moves slightly to the right, thereby applying tension to the person's lower back.

Figure 4A:
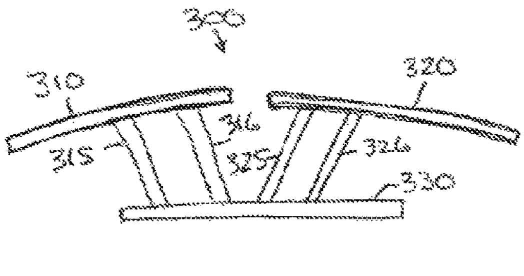
FIGS. 4A and 4B are diagrams illustrating a third exemplary embodiment of a lumbar traction device having a split back support.
Figure 4B:
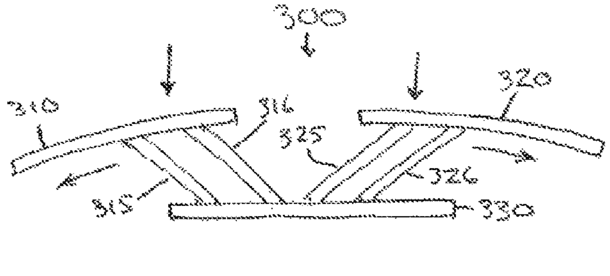

Referring to FIGS. 4A and 4B, another alternative embodiment of a lumbar traction device is shown. In this embodiment, lumbar traction device 300 includes a lower back support portion 310 and an upper back support portion 320. Each of these back support components is movably connected to base 330. Lower back support 310 is connected to the base by movable supports 315 and 316, while upper back support 320 is connected to the base by movable supports 325 and 326.

Traction device 300 is intended to be placed on a support surface such as the floor and positioned with the gap between lower back support 310 and upper back support 320 in the small of the user's back. When no weight is placed on either of supports 310 or 320, they are positioned as shown in FIG. 4A. As the person's weight is placed on the device, the back support components (310, 320) are pushed downward, causing movable supports 315, 316, 325 and 326 to pivot outward, away from the center of the device, as shown in FIG. 4B. This causes lower back support 310 and upper back support 320 to move away from each other, thereby applying tension to the person's lower back.

Figure 5:
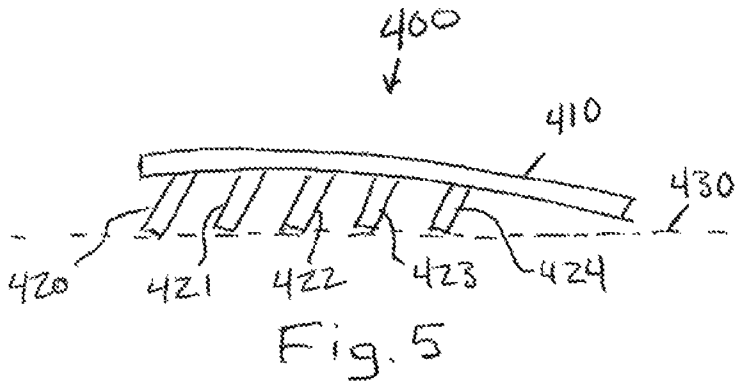
FIG. 5 is a diagram illustrating a fourth exemplary embodiment of a lumbar traction device having a flexible support structure.

Referring to FIG. 5, another alternative embodiment of a lumbar traction device is shown. In this embodiment, device 400 has a back support 410 which has several movable supports or legs 420-424 attached to its underside. In this embodiment, device 400 is positioned with the left end of the device in the small of the user's back as the user reclines on a support surface such as the floor (430) in the same orientation as shown in FIG. 1. In this embodiment, the floor effectively serves as the base on which the support structure pivots. When the movable supports (420-424) are in contact with the support surface and the person's weight is applied to back support 410, the movable supports flex or pivot (clockwise), causing the back support to move to the right. It is assumed that the person's lower body (e.g. hips) will be in contact with the floor, and will therefore tend to remain stationary, while the person's torso is urged to the right. This provides tension between the torso and lower body, thereby relieving compression on the vertebrae and discs in the lower back.

The benefits and advantages which may be provided by the present invention have been described above with regard to specific embodiments. These benefits and advantages, and any elements or limitations that may cause them to occur or to become more pronounced are not to be construed as critical, required, or essential features of any or all of the claims. As used herein, the terms "comprises," "comprising," or any other variations thereof, are intended to be interpreted as non-exclusively including the elements or limitations which follow those terms. Accordingly, a system, method, or other embodiment that comprises a set of elements is not limited to only those elements, and may include other elements not expressly listed or inherent to the claimed embodiment.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed within the following claims.

What is claimed is:

1. A lumbar traction device comprising:

a back support;

a base; and a movable support structure connected between the base and an underside of the back support, wherein the movable support structure enables the back support to move with respect to the base;

wherein when a user lies on the lumbar traction device with the user's hips on the base and the user's back on the back support, the user's weight causes the movable support structure to move downward, thereby causing the back support to move in a direction that applies tension to the user's back away from the user's hips and wherein when the user's weight is removed from the lumbar traction device, the movable support structure returns to a more upright position.

2. The lumbar traction device of claim 1, wherein the base comprises a flat structural member.

3. The lumbar traction device of claim 1, wherein the movable support structure is pivotally connected to the base.

4. The lumbar traction device of claim 3, wherein the movable support structure is pivotally connected to the back support.

5. A method comprising:

providing a device having a back support, wherein the back support is connected to a movable support structure that rests on a base, wherein the back support is movable with respect to the base; and positioning a user on the device, wherein the user's hips rest on the base and the user's back rests on the back support;

wherein the user's hips are held in position on the base, and wherein when a user lies on top of the device, the user's weight causes the back support to move on the movable support structure in a direction away from the user's hips that applies tension to the user's back and wherein when the user's weight is removed from the device, the back support moves on the movable support structure is a direction toward the user's hip.

6. The method of claim 5, wherein the base comprises a flat surface.

7. A method comprising:

providing a device having a back support, wherein the back support is connected to a movable support structure that rests on a base, wherein the back support is movable with respect to the base; and positioning a user on the device, wherein the user's hips rest on a first portion of the base and the user's back rests on the back support;

wherein the user's hips are held in position on the first portion of the base, and wherein when a user lies on top of the device, the user's weight causes the back support to move in a direction away from the user's hips on the first portion of the base that applies tension to the user's back and wherein when the user's weight is removed from the device, the back support moves a direction toward the user's hip away from the user's hips; and wherein the movable support structure pivots on the base.

* * * * *